(12) United States Patent
Feckler (10) Patent No.: US 8,653,239 B2
(45) Date of Patent: Feb. 18, 2014

(54) METHOD FOR ISOLATING POLYPEPTIDES

(75) Inventor: Christian Feckler, Aachen (DE)

(73) Assignee: Qiagen GmbH, Hilden (DE)

( * ) Notice: Subject to any disclaimer, the term of this patent is extended or adjusted under 35 U.S.C. 154(b) by 387 days.

(21) Appl. No.: 12/988,116

(22) PCT Filed: Apr. 9, 2009

(86) PCT No.: PCT/EP2009/002637
§ 371 (c)(1),
(2), (4) Date: Nov. 19, 2010

(87) PCT Pub. No.: WO2009/127359
PCT Pub. Date: Oct. 22, 2009

(65) Prior Publication Data
US 2011/0065897 A1  Mar. 17, 2011

(30) Foreign Application Priority Data

Apr. 16, 2008 (DE) .......................... 10 2008 019 338

(51) Int. Cl.
| | | |
|---|---|---|
| *A61K 38/00* | (2006.01) | |
| *C07K 1/00* | (2006.01) | |
| *B01J 27/24* | (2006.01) | |
| *A23J 1/00* | (2006.01) | |
| *C07K 14/00* | (2006.01) | |
| *C07K 16/00* | (2006.01) | |
| *C07K 17/00* | (2006.01) | |

(52) U.S. Cl.
USPC ............ 530/344; 423/291; 502/400; 530/417

(58) Field of Classification Search
None
See application file for complete search history.

(56) References Cited

U.S. PATENT DOCUMENTS

| | | | | |
|---|---|---|---|---|
| 3,869,374 A | * | 3/1975 | Goldacker et al. | ............ 204/273 |
| 4,287,259 A | * | 9/1981 | Riley et al. | ................... 428/408 |
| 4,946,713 A | * | 8/1990 | Sneddon et al. | ............... 427/226 |
| 5,356,850 A | * | 10/1994 | Correia et al. | ................ 502/185 |
| 5,509,041 A | * | 4/1996 | Resnick et al. | ................. 378/34 |
| 6,478,994 B1 | * | 11/2002 | Sneddon et al. | ................ 264/43 |
| 6,614,869 B1 | * | 9/2003 | Thibieroz et al. | ............. 376/333 |
| 2002/0028520 A1 | * | 3/2002 | Boschetti et al. | ............. 436/518 |

FOREIGN PATENT DOCUMENTS

DE  19926056  3/2004

OTHER PUBLICATIONS

Mortensen et al. Functionalization and Cellular Uptake of Boron Carbide Nanoparticles. The First Step toward T Cell-Guided Boron Neutron Capture Therapy. Bioconjugate Chem. Published on Web Feb. 17, 2006. vol. 17, pp. 284-290.*
HEPES solution: http://www.sigmaaldrich.com/etc/medialib/docs/Sigma/Product_Information_Sheet/2/h0887pis.Par.0001.File.tmp/h0887pis.pdf, accessed online Jan. 8, 2013, last update Nov. 2003, 2 pages.*
Thevenot. Boron carbide- A comprehensive review. Journal of European Ceramic Society. 1990. vol. 6, No. 4, pp. 205-225.*
Nordstrom, et al., "Generation of a New Protein Purification Matrix by Loading Ceramic Hydroxyapatite with Metal Ions-Demonstration with Poly-Histidine Tagged Green Fluorescent Protein", Journal of Biotechnology, Jan. 1, 1999, vol. 69, pp. 125-133.
Aldington, et al., "Scale-Up of Monoclonal Antibody Purification Processes", Journal of Chromatography B: Biomedical Sciences & Applications, Mar. 12, 2007, vol. 848, No. 1, pp. 64-78.

\* cited by examiner

*Primary Examiner* — Marcela M Cordero Garcia
(74) *Attorney, Agent, or Firm* — Fanelli Haag & Kilger PLLC

(57) ABSTRACT

The present invention relates to a method for isolating and/or purifying at least one polypeptide from a polypeptide-containing sample, characterized in that the sample is contacted with a boron carbide support material at a pH which allows the binding of the polypeptide to the boron carbide support material. Such isolating can, for example, be used to remove polypeptides from a sample or else to purify and/or to concentrate polypeptides. A matrix comprising a boron carbide support material for purification of polypeptides is further disclosed according to the invention.

16 Claims, 7 Drawing Sheets

Figure 4 a) Plasma (Coomassie staining)

b) Urine (silver staining)

METHOD FOR ISOLATING POLYPEPTIDES

The present invention relates to a method for purifying polypeptides by using boron carbide support materials.

Purifying proteins from heterogeneous mixtures is often a multistep process using the physical, chemical, and electrical properties of the proteins to be purified. Important characteristics of a protein which are relevant for the purification are the solubility, the charge, the size, and the specific binding capacity. The isolation and cleanup of proteins is therefore a particular challenge, owing to the different chemical and physical properties of these biomolecules. Also, the materials from which the proteins are isolated and also the subsequent applications of the isolated proteins are diverse. It is therefore necessary to extend the already existing techniques for purifying and isolating proteins.

An established principle for isolating polypeptides/proteins is solid-phase extraction (SPE). The analyte (polypeptide/protein) is bound to a solid support and, after washing, eluted. A disadvantage of existing SPE systems is the binding under strongly acidic conditions (for example, pH<1.5) and the elution with organic solvents, such as acetonitrile (ACN). These conditions can have a denaturing effect on the proteins and thus impair the application and analysis possibilities of the isolated proteins. In addition, ACN is a solvent which is classified as dangerous and which must also be removed for many subsequent analytical techniques.

In addition to the established SPE products which are based on reversed-phase chemistry, such as, for example, C18 materials, there are also SPE systems which are based on a silicon carbide ceramic foundation (see, for example, WO 03/044043). The binding of protein to the solid phase is likewise achieved here by acidification, i.e., protonation of the proteins.

Therefore, an object of the present invention is to provide suitable methods and also suitable solid phases for isolating, more particularly purifying and/or removing, polypeptides from a sample.

According to the invention, there is provided a method for isolating and/or purifying at least one polypeptide from a polypeptide-comprising sample, characterized in that the polypeptide-containing sample is contacted with a boron carbide support material at a pH which allows the binding of the polypeptide to the boron carbide support material.

It was found that, surprisingly, boron carbide has particularly good polypeptide-binding properties. Thus, as the examples show, both peptides and proteins can be bound; furthermore, phosphorylated peptides can also bind effectively and thus be isolated, purified, and/or concentrated.

The method according to the invention can be used to remove polypeptides from a sample. The targeted removal of polypeptides can, for example, be advantageous by making it possible to more easily analyze or investigate other biomolecules, such as, for example, nucleic acids, or smaller organic molecules, such as, for example, drugs or metabolites, without the interference of polypeptide impurities. The method according to the invention for isolating at least one polypeptide therefore also comprises embodiments in which polypeptides are removed from a sample. The polypeptides to be removed from the sample bind to the boron carbide support material and are thus present in a lower amount, if at all, in the flow-through (when using a boron carbide column) or in the supernatant (for example, when using magnetic particles with a boron carbide surface). If desired, the polypeptide can in this case also be eluted from the boron carbide support material in order to further process, for example, to analyze, the polypeptide fraction away from the rest of the sample.

The use of boron carbide as a support material for binding polypeptides works essentially according to the principle of solid-phase extraction (SPE). The polypeptides adsorb to the boron carbide support material, presumably by ionic interactions.

Preferably, the polypeptides bind to the boron carbide support material at a pH which is below the pI of the polypeptide(s) to be bound. Preferably, binding takes place at a pH which is at least 0.5 pH units below the pI. The isoelectric point (pI) of the polypeptide to be isolated can be determined by known techniques, such as, for example, isoelectric focusing in a polyacrylamide gel. The isoelectric point can, however, also be roughly determined by predictive techniques, for example, by analysis of the amino acid composition and of the calculation of the charges of the ionizable groups at various pH's using the Henderson-Hasselbach equation.

Preferably, binding takes place at an acidic pH. At an acidic pH, more particularly many different polypeptides can be effectively bound and thus isolated. The acidic binding pH can, for example, be set by adding acid-containing solutions or acidic buffers to the polypeptide-containing sample in order to acidify it to the desired pH.

In a further embodiment, the boron carbide support material is equilibrated at an acidic pH before it is contacted with the polypeptide-containing sample. Through the equilibration, the boron carbide support material is optimally prepared for the binding of the polypeptides.

Preferably, the binding pH in the sample mix is $\leq 6$, $\leq 5$, $\leq 4.5$, $\leq 4$, or even $\leq 3.5$. However, the pH is preferably above 1.5 and more preferably above 2.5 in order to avoid too strongly acidic conditions which could have a denaturing effect on the polypeptides.

Appropriate acidic conditions are preferably set during the binding of the polypeptides to the boron carbide support material in the polypeptide-containing sample mix and also for equilibrating the boron carbide support material (if carried out).

In contrast, the polypeptide or polypeptides bound to the boron carbide support material is/are preferably eluted at a pH which is above the pI of the polypeptide to be eluted. Preferably, the pH is one pH unit above the isoelectric point (pI).

Preferably, the elution pH is alkaline and is $\geq 9$, $\geq 10$, and more preferably $\geq 11$. At a pH $\geq 11$, particularly good results were achieved in elution from the boron carbide support material according to the invention.

To set the pH, acid- or base-containing solutions can, as explained, be used. Furthermore, acidic or basic buffers can also be used as solutions. Examples of acidic buffers are, for example, acetate buffer, citrate buffer, or glycine buffer. Established basic buffers are, for example, Tris buffer, bicine buffer, TAPS buffer, or tricine buffer.

The term "polypeptide" refers to a polymer of amino acids which are linked via peptide bonds. The term "polypeptide" encompasses polypeptides of any length, including proteins (with a length of more than 50 amino acids) and also peptides (with a length of 2 to 49 amino acids). According to the invention, one or more polypeptides can be isolated, purified, concentrated, and/or removed from a sample.

The sample from which the polypeptides are isolated can be of any kind. For example, mention may be made of polypeptide-containing solutions, body fluids such as plasma, urine, semen, teardrops, saliva, and cerebrospinal fluid. Furthermore, polypeptides can also be isolated from cell-containing samples, such as, for example, cell lysates or polypeptide-containing culture media. Particularly problematic is the isolation of polypeptides from diluted and particularly salt-containing samples, such as, for example, urine. With such solutions/samples, the method according to the invention delivers particularly good results.

In addition to the method according to the invention for isolating polypeptides from polypeptide-containing samples, there is further provided a matrix for binding polypeptides, characterized in that it comprises boron carbide. The matrix can ultimately be present in a variety of forms, for instance as a column, a membrane, beads, more particularly magnetic beads, and also as a chip surface. What is ultimately decisive is that the matrix comprise a boron carbide-containing surface or adsorption surface which is accessible from the sample for the binding of the polypeptides.

The matrix according to the invention can, for example, be in the form of a column body. Preferably, the column body includes an inlay for accommodating the boron carbide support material. It has become apparent that the geometry of such a column body can also be important for the effectiveness of polypeptide binding from the sample. This more particularly when the sample comprises a multiplicity and more particularly also different polypeptides. In such a case, highly effective binding of the polypeptides to the boron carbide support material is necessary in order to comprehensively remove the polypeptides from the sample. Here, it has become apparent that it is particularly advantageous to make the cross-section of the boron carbide support material as narrow as possible and the contact pathway of the sample with the boron carbide support material as long as possible. For this reason, the column body is preferably distinctly longer than it is wide. The inlay, accommodating the boron carbide support material, of the column is at least twice as long as it is wide, preferably 3, 4, 5, or at least 6 times as long. Through this configuration, the sample upon passing through the boron carbide support material remains in contact for as long as possible with the support material over a long distance, whereby the polypeptides are particularly effectively bound. As the examples prove, a corresponding column geometry leads to distinctly improved results. More polypeptides become bound from the sample, and so fewer polypeptides are found in the flow-through.

The invention further provides a method for producing a column body, characterized in that a column body with an inlay of the above-described geometry is loaded with a boron carbide support material. Loading can, for example, be achieved by introducing dry boron carbide powder into the inlay. By using a plunger, the boron carbide support material can be densely packed.

The present invention further provides for the use of a boron carbide support material or a matrix as described above for binding polypeptides.

There is further provided a kit for isolating polypeptides from a polypeptide-comprising sample, characterized in that it includes a boron carbide-containing matrix. Details about the boron carbide-containing matrix are described in detail above; we refer to our above explanations.

The kit according to the invention can further include one or more of the following constituents:
an acidic binding and/or equilibration buffer,
a preferably alkaline elution buffer The method according to the invention can, for example, be carried out by generating a slurry of the polypeptide-containing sample (if necessary, opened up by lysis) and the boron carbide support material at the above-described binding pH. The boron carbide can, for example, be removed from the mixture after the polypeptide becomes bound. Alternatively, unbound constituents can be removed by centrifugation. Elution can, for example, be achieved by producing a slurry of the boron carbide with a suitable elution solution. An elution buffer can also be used. Suitable elution conditions are described in detail above.

Alternatively, the boron carbide can be introduced into a column body and set or equilibrated to the desired binding pH. The polypeptide-containing sample, which is set to the desired binding pH, is added in a conventional way over the column. After polypeptide binding, elution is effected with the desired elution solution or at the desired elution pH.

In a further embodiment, the boron carbide, preferably equilibrated to the desired binding pH, can be added to a spin column. The polypeptide-containing sample, which is set to the desired linking pH, is added to the surface of the boron carbide support material. The column is spun in order to separate the aqueous phase; the aqueous phase is discarded. The protein bound to the boron carbide support material is washed and eluted at the desired pH. This is achieved by adding the desired elution solution in order to set the elution pH, followed by a spin step in order to elute the aqueous phase comprising the isolated protein.

The use of spin columns is unproblematic in the use of the boron carbide support material according to the invention, since boron carbide withstands centrifugation forces well.

DESCRIPTION OF THE FIGURES

FIGS 1a and 1b:

The polypeptide-binding capacity of various potential support materials is shown (silicon nitrite (alpha), silicon nitride (beta), boron nitride, and boron carbide). Results of the gel electrophoresis are shown. A 12% Laemmli polyacrylamide gel was used; staining was done with Coomassie Brilliant Blue. As shown particularly in FIG 1b, only boron carbide is capable of effectively binding polypeptides and thus removing polypeptides from a polypeptide-containing sample, and of releasing the polypeptides again upon elution.

FT: Flow-through

E: Eluate

FIG. 2:

The influence of column geometry on the purification behavior of the boron carbide support material is shown. With the tested column with an inlay (whereby a column geometry was achieved in which the length of the boron carbide column was about 5 times as long as it was wide, it was possible to achieve distinctly better binding and elution results than with a column without an inlay.

FT: Flow-through

E: Eluates

FIG. 3:

The column geometry according to an advantageous embodiment is shown. Preferably, the outer circumference of the column body (1) features a funnel-shaped taper (2) so that the boron carbide support material can be introduced more easily into the inlay (3). About 50 to 60 mg of boron carbide fit into the embodiment shown. This boron carbide is spun in order to bring it into a compact form and to compress it accordingly.

FIGS. 4a and 4b:

The results of the binding of proteins to the boron carbide support material from plasma and urine samples are shown. The results of the gel electrophoresis are shown. Figure a shows the results of a Coomassie staining in the purification of polypeptides from plasma. Figure b shows the results of the polypeptide purification from a urine sample with the aid of silver staining. Silver staining has high sensitivity in comparison with Coomassie stained gels.

M: Marker
P: Plasma
ST: Flow-through
E: Eluates

FIGS. 5a and 5b:

FIG. 5a shows the yield of phosphorylated polypeptides (100 µg) from various samples. First, phosphorylated proteins were isolated with the help of an affinity column (PhosphoProteinPurification Kit, QIAGEN), and then the eluate was concentrated. The method according to the invention, using boron carbide, was compared with a method according to the prior art (Nanosep). FIG. 5b shows the results of a Western blot. Per lane, 10 µg of protein were applied. The eluate of the PhosphoProtein Purification column concentrated with Nanosep ultrafiltration columns was in the output. The experiment was carried out in duplicate.

FIGS. 6a and 6b:

The results of the isolation of peptides (here, of beta-galactosidase) with the method according to the invention are shown.

EXAMPLES

The invention will now be eludicated by means of illustrative examples. These examples solely serve to elucidate the invention in more detail; they are not limiting.

Example 1

Protocol For Carrying Out the Method According To the Invention

Unless otherwise specified, 60 mg of boron carbide or other ceramics were weighed and filled into spin columns. The columns were equilibrated with 50 mM glycine, pH 3.5. The protein solution was adjusted with 1 M glycine, pH 1.5, to a pH of 3.5 and added to the spin column. This was followed by either incubation by mixing for 30 minutes, or, in the case of use of the inlay, direct spinning.

The bound polypeptides were washed with 50 mM glycine, pH 3.5. Elution was with 10 mM Tris, pH 12.

Example 2

Boron Carbide in Comparison With Other Ceramics

Four different ceramics (silicon nitride (alpha), silicon nitride (beta), boron nitride, and boron carbide) were investigated for their polypeptide-binding capacity. Plasma was used as a polypeptide-containing sample; procedure was according to the protocol of example 1. Only boron carbide shows binding of the plasma proteins with successful elution.

Figure 1:
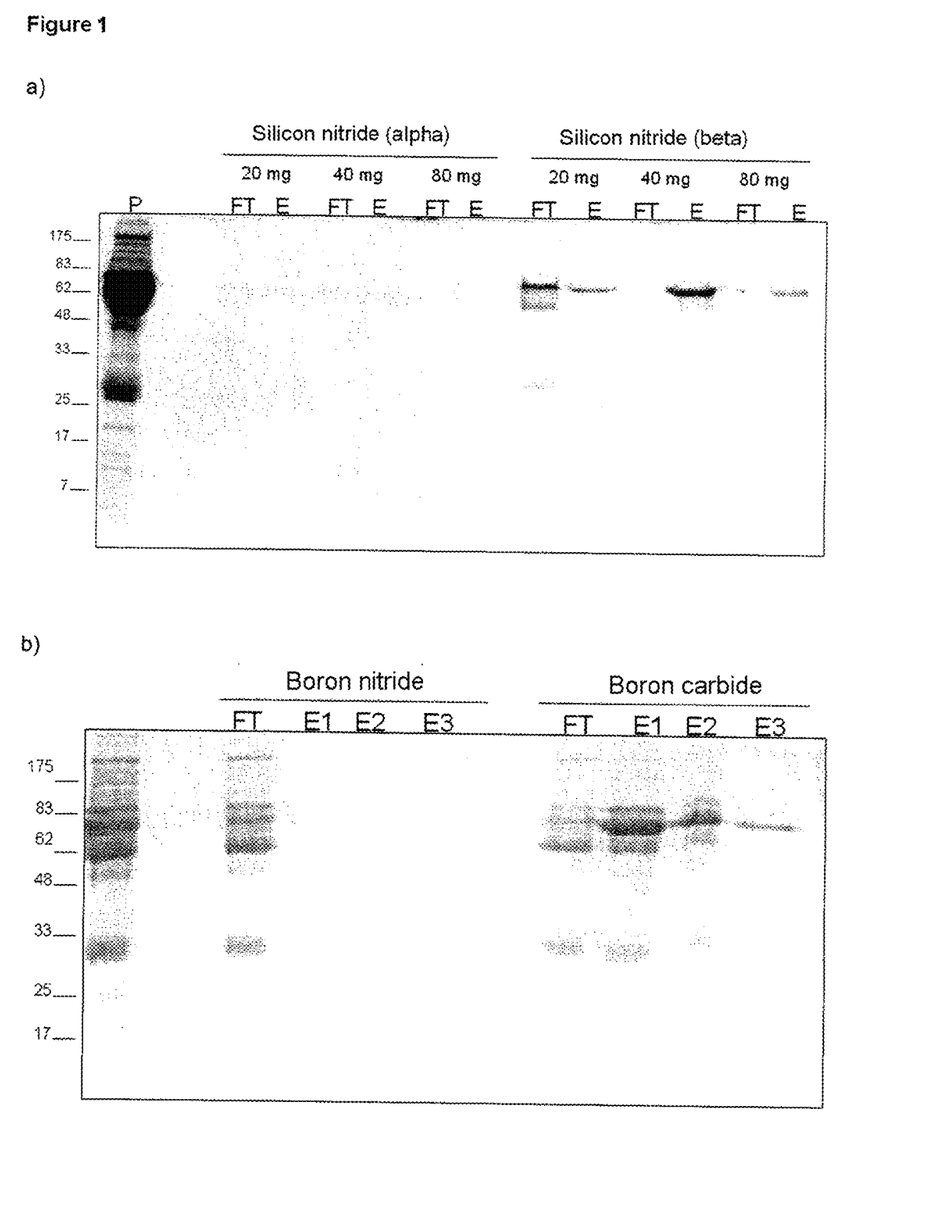

FIG. 1 shows the results.

Example 2

Influence of the Geometry of the Column Body (Compressed Powder)

Figure 2:
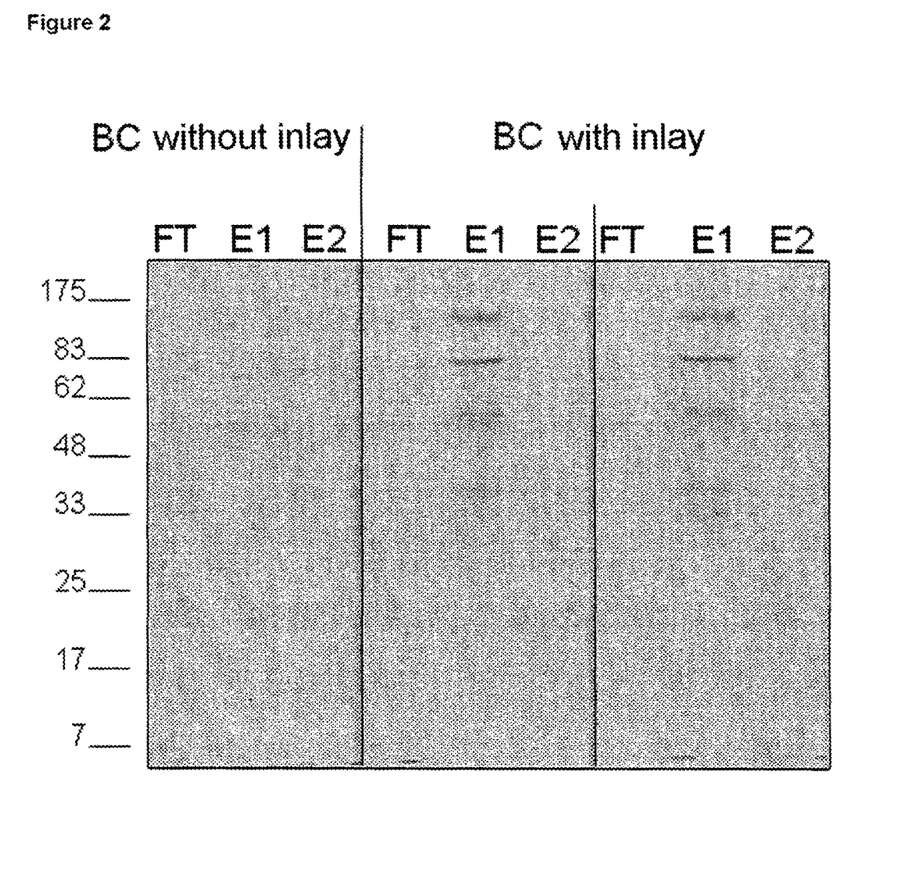
Figure 3A:
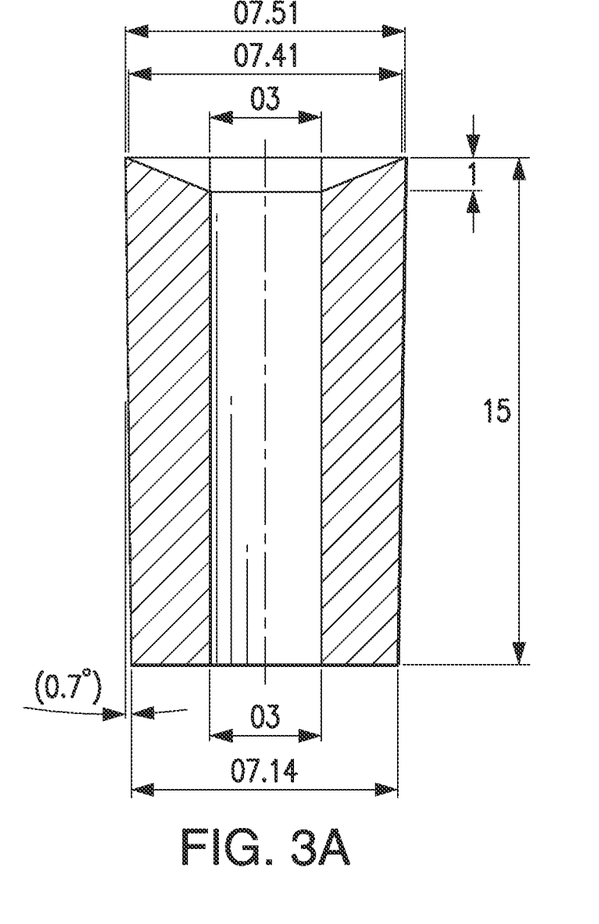
Figure 3B:
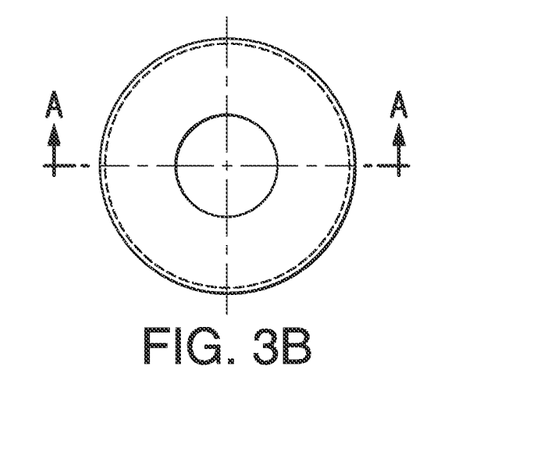

During the tests, it was observed that changing the column geometry (reducing the column inner diameter) made it possible to achieve an improved recovery and thus yield of the proteins (see FIG. 2). In order to carry out the reduction of the column inner diameter, a small plastic tube was designed which was introduced into the existing column bodies (DyeEx spin column) (FIG. 3). The ceramic powder was filled into this small inner tube and compressed. As a result, the sample is led over the entire/extended distance of the elongate column body, whereby the binding of the polypeptides is distinctly improved.

Example 3

Use of Various Polypeptide-Containing Sample Materials

Figure 4:
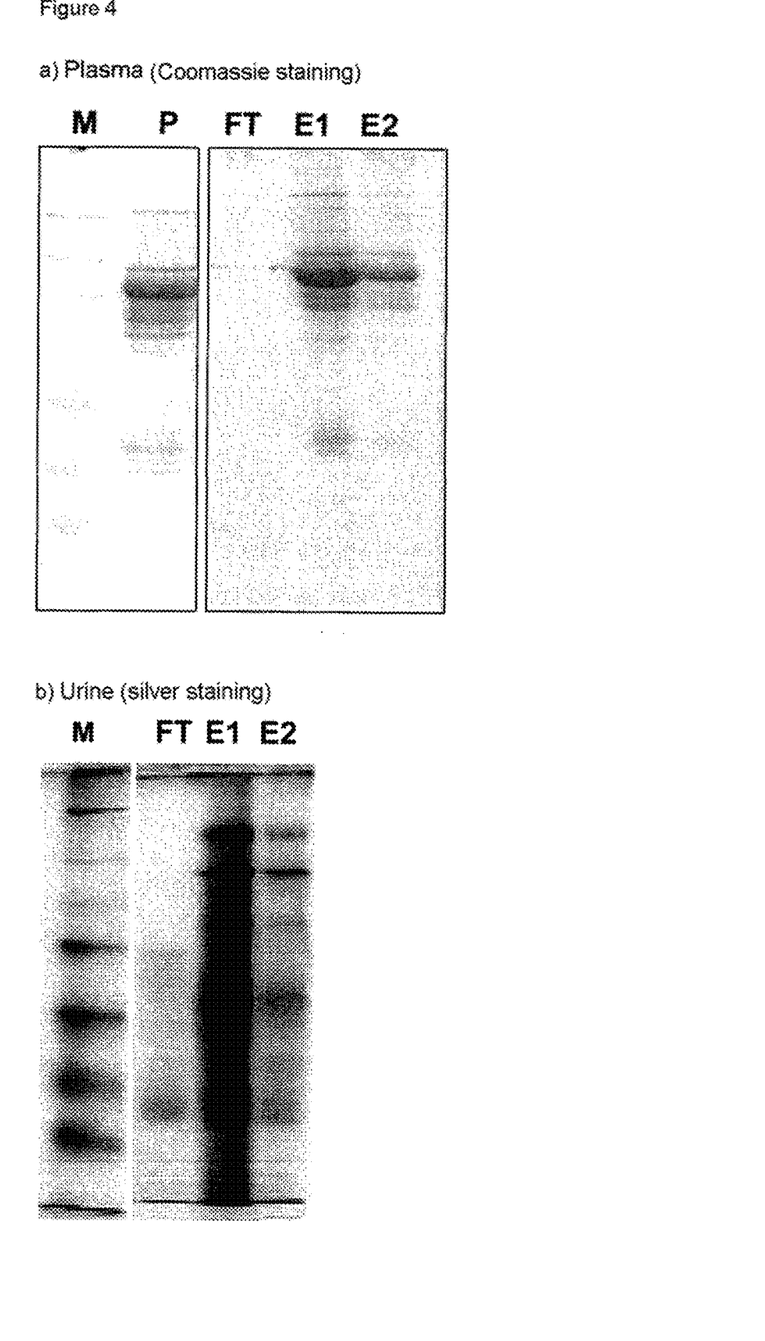

The applications shown in FIG. 4 prove that, with the method according to the invention, proteins can be specifically isolated from different polypeptide-containing samples. In A), diluted plasma was used; in B), 1 ml urine was used.

Example 4

Isolation of Phosphorylated Proteins

Figure 5:
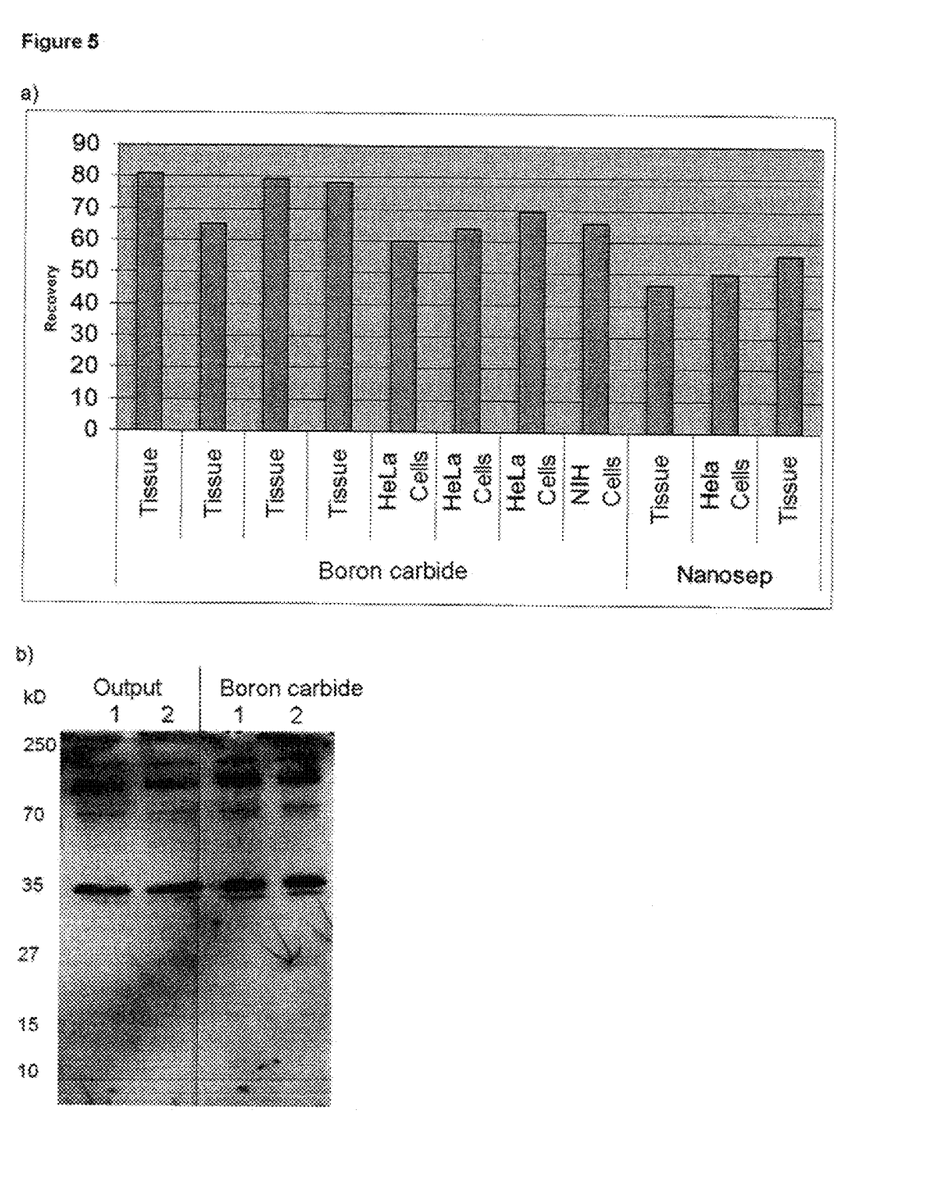
Figure 6A:
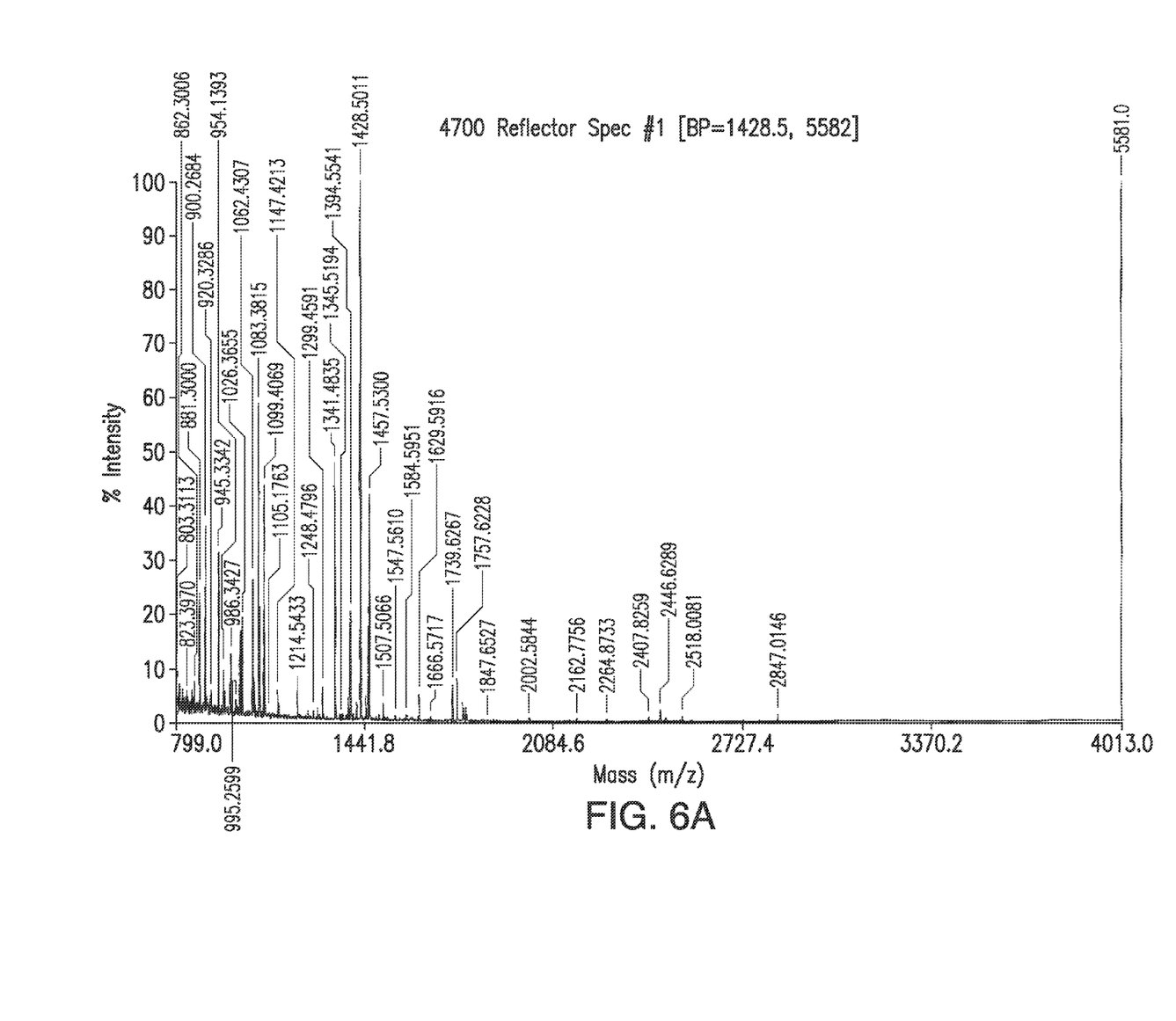
FIG. 6a shows the MALDI-TOF-MS results in the eluate of the boron carbide column. Figure b shows the peptides present in the flow-through of the column (no significant amounts).
Figure 6B:
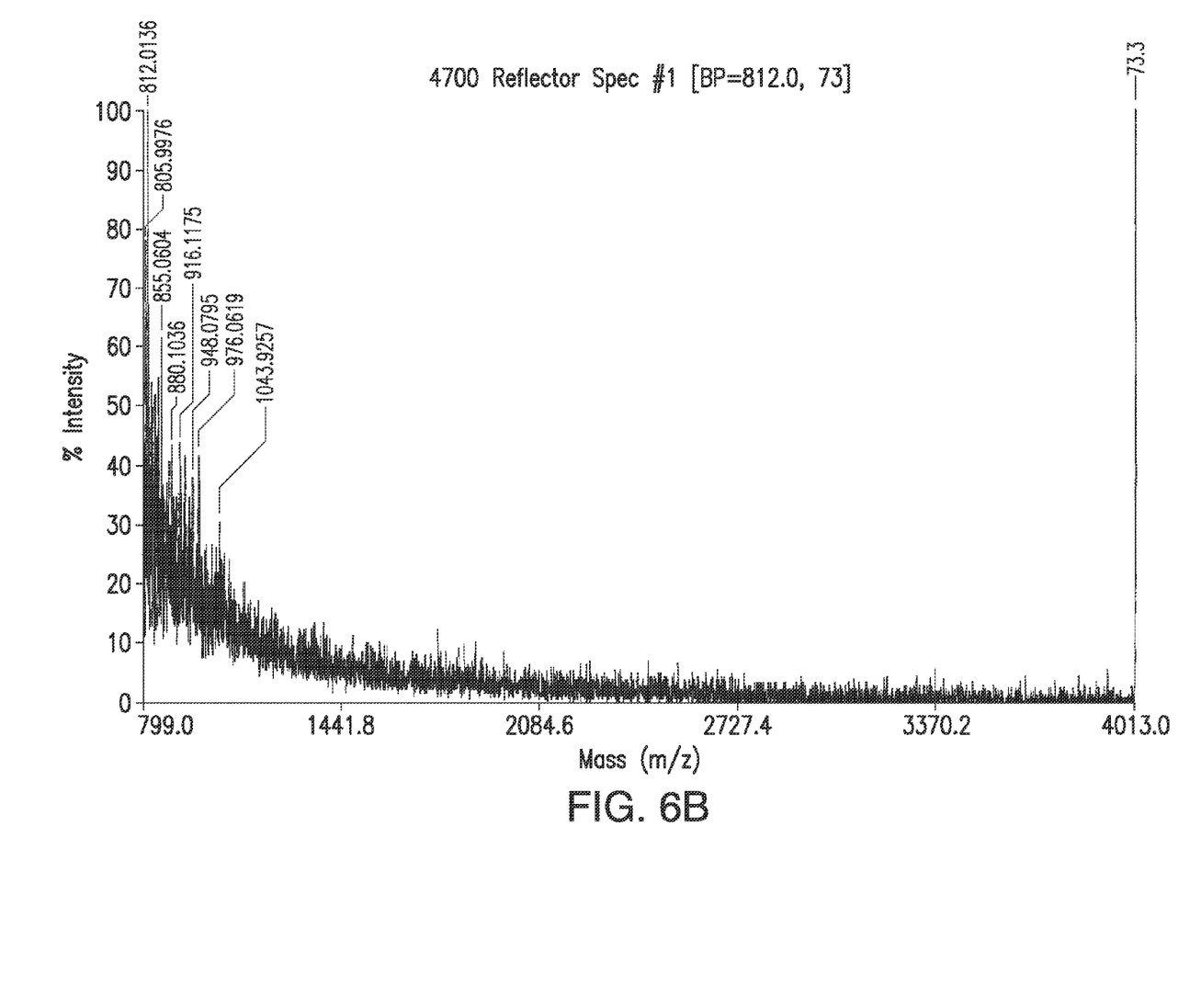

After the isolation of phosphorylated proteins with the PhosphoProteinPurification Kit (QIAGEN), 100 µg of the eluates were bound in each case over a boron carbide column (with about 60 mg of powder) and eluted. The yield is about 60-80%. In comparison to this, the protein solution was concentrated with an established ultrafiltration column. The recovery here is <60% (FIG. 5A).

In the Western blot experiment (FIG. 5B), the identity of the phosphorylated proteins were confirmed. An anti-phosphotyrosine antibody (4G10) was used.

In the present case, the PhosphoKit was used beforehand in order to demonstrate the particular efficiency of the method in the purification of phosphoproteins. A corresponding efficiency is also achieved in the purification from a mixed sample (phosphorylated and nonphosphorylated proteins or peptides).

Example 5

Isolation of Peptides

In order to check whether the method according to the invention can also be used for isolating peptides, a peptide mixture (tryptic fragments of (β-galactosidase) was processed. Through MALDI-TOF-MS, it was possible to demonstrate that, except for one peptide, it was possible to bind and elute all peptides of the mixture. In the flow-through, it was not possible to detect significant amounts of peptide. The method is therefore also very highly suitable for isolating smaller peptides from a sample.

The invention claimed is:

1. A method for isolating and/or purifying at least one polypeptide from a polypeptide-containing sample, wherein the sample is contacted with a boron carbide support material at a pH which allows the binding of the polypeptide to the boron carbide support material.

2. The method as claimed in claim 1, wherein the at least one polypeptide is isolated in order to remove it from the sample.

3. The method as claimed in claim 1, wherein the at least one polypeptide is eluted from the boron carbide support material.

4. The method as claimed in 1, wherein binding takes place at a pH which is below the pI of the polypeptide to be bound.

5. The method as claimed in claim 1, wherein binding takes place at an acidic pH.

6. The method as claimed in claim 1, wherein the boron carbide support material is equilibrated at an acidic pH.

7. The method as claimed in claim 5, wherein the pH is ≤6, ≤5, ≤4.5, ≤4, or ≤3.5.

8. The method as claimed in claim 1, wherein the at least one polypeptide is eluted at a pH which is above the pI of the polypeptide to be eluted.

9. The method as claimed in claim 8, wherein the pH is ≤9, ≤10, or ≤11.

10. The method as claimed in claim 1, wherein the sample is selected from the group consisting of salt-containing solutions, body fluids, plasma, urine, cell lysates, semen, teardrops, sweat, saliva, and cerebrospinal fluid.

11. A matrix for binding polypeptides, comprising boron carbide support material and a column body, wherein the boron carbide support material has been equilibrated at an acidic pH and has a surface accessible to a sample comprising polypeptides, and wherein the column body features an inlay for accommodating the boron carbide support material.

12. The matrix as claimed in claim 11, wherein the inlay of the column body is at least twice as long as it is wide.

13. A method for producing a matrix as claimed in claim 12, comprising loading the inlay with the boron carbide support material.

14. A kit for purifying and/or isolating polypeptides, comprising a matrix as claimed in claim 11.

15. The kit as claimed in claim 14, comprising one or more of the following constituents: (a) an acidic binding and/or equilibration buffer and (b) an alkaline elution buffer.

16. The matrix as claimed in claim 12, wherein the inlay of the column body is about 3 times as long to about 6 times as long as it is wide.

* * * * *